United States Patent [19]
Bareket

[11] Patent Number: 5,889,593
[45] Date of Patent: Mar. 30, 1999

[54] OPTICAL SYSTEM AND METHOD FOR ANGLE-DEPENDENT REFLECTION OR TRANSMISSION MEASUREMENT

[75] Inventor: Noah Bareket, Saratoga, Calif.

[73] Assignee: KLA Instruments Corporation, San Jose, Calif.

[21] Appl. No.: 806,347

[22] Filed: Feb. 26, 1997

[51] Int. Cl.[6] ................................................ G01N 21/55
[52] U.S. Cl. ........................................................ 356/445
[58] Field of Search ..................... 356/445, 446, 356/425, 324, 373, 2, 4, 5, 375, 376, 71, 399–401; 250/559.16, 559.18, 227.2, 227.23, 227.24, 227.29, 458.1, 459.1, 461.1, 571; 385/116, 119, 121, 120

[56] References Cited

U.S. PATENT DOCUMENTS

| | | | |
|---|---|---|---|
| 4,619,508 | 10/1986 | Shibuya ................................... | 353/122 |
| 4,710,642 | 12/1987 | McNeil .................................... | 250/571 |
| 4,999,014 | 3/1991 | Gold et al. ............................... | 356/382 |
| 5,022,087 | 6/1991 | Peppers et al. .......................... | 382/32 |
| 5,028,802 | 7/1991 | Webb et al. ............................. | 250/571 |
| 5,099,131 | 3/1992 | Brownrigg et al. ................. | 250/458.1 |
| 5,164,790 | 11/1992 | McNeil et al. .......................... | 356/355 |
| 5,225,876 | 7/1993 | Lux et al. ................................ | 354/403 |
| 5,610,719 | 3/1997 | Allen et al. .............................. | 356/374 |
| 5,699,447 | 12/1997 | Alumot et al. .......................... | 382/145 |
| 5,701,181 | 12/1997 | Boiarski .................................. | 356/446 |

OTHER PUBLICATIONS

S. S. H. Naqvi et al., "Etch depth estimation of large–period silicon gratings with multivariate calibration of rigorously simulated diffraction profiles", *J. Opt. Soc. Am. A*, vol. 11, No. 9, pp. 2485–2493 (Sep. 1994).

Doh Hoon Kim et al., "Probe beam scan type auto–focus system using position sensing detector for sub–half micron lithography tools", *Proc. SPIE*, vol. 2726, pp. 876–885 (1996).

Michael Bass et al., *Handbooks of Optics*, vol. I and II, Chapters 7 and 26, pp. 7.1–7.13 and 26.1–26.16, McGraw–Hill, Inc., New York, N.Y. (1995).

*Primary Examiner*—Frank G. Font
*Assistant Examiner*—Michael P. Stafira
*Attorney, Agent, or Firm*—Thomas Schneck; Mark Protsik

[57] ABSTRACT

An angle-dependent reflectometer or transmissometer includes an optical imaging array in the incident and reflected or transmitted light path that breaks up an incident light beam into mutually spatially incoherent light bundles. The individual light bundles are then focused to a common spot by a high numerical aperture objective lens so as to provide a range of incidence angles on a sample surface. In a reflectometer, reflected light returns through the objective lens and imaging array and is imaged onto a detector array where different incidence and reflection angles are received by different groups of detection elements. In the angle-dependent transmissometer, the imaging array and high numerical aperture focusing objective lens are used for illuminating a spot on the sample, with a second high numerical aperture collection objective lens and detector array used for receiving transmitted light over a wide range of collection angles. The angle-dependent reflectance or transmittance measurement provided by the detector array can be analyzed to determine a desired characteristic parameter of the illuminated area of the sample surface. For example, a periodic text pattern on a wafer or mask surface can be illuminated to obtain a linewidth measurement. The break up of the light by the imaging array into light bundles allows the spot size to be controlled independently of the range of illumination angles so that areas much larger than the diffraction limit can be illuminated.

38 Claims, 5 Drawing Sheets

OPTICAL SYSTEM AND METHOD FOR ANGLE-DEPENDENT REFLECTION OR TRANSMISSION MEASUREMENT

TECHNICAL FIELD

The present invention relates to optical systems for measuring dimensions (e.g., width or thickness) or profile of features, such as deposited and etched lines, formed on a reflective wafer surface or on a transmissive surface, and in particular, to systems that measure light reflection or transmission from periodic patterns that are formed on the surface as microscopic features or calibration reference targets or as an aid to process monitoring.

BACKGROUND ART

There are a variety of optical measuring and testing applications in which light is incident upon a surface and then selected parameters of the reflected or transmitted light, such as intensity or polarization, are measured. Thus, it may be desired to measure surface roughness, thin film layer thickness, etch depth of various surface structures, or linewidth. Various common techniques include spectrometry, interferometry, polarimetry, ellipsometry, scatterometry, reflectometry and transmissometry. For example, one way to measure the dimensions (width or thickness) and shape of lines formed on a generally flat, reflective semiconductor wafer surface is to provide a test pattern of such lines formed as a high frequency grating in designated areas on the wafer surface interspersed among the integrated circuit patterns, then to illuminate the test pattern with monochromatic light from a laser source, and to detect and measure the resulting reflectance at various angles. From an analysis of the measured angle-dependent reflectance data, for example by comparison with reference data obtained from either a theoretical model or previous measurements done on calibration standards, the desired line parameter or parameters can be determined.

Figure 1:
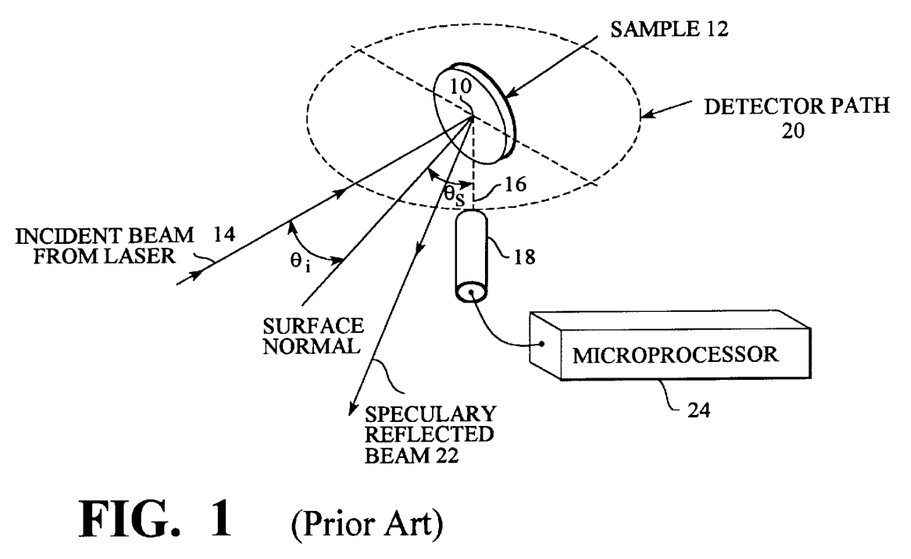
FIG. 1 is a perspective diagram of a first surface inspection instrument of the prior art carrying out scatterometry on a sample surface with direct collimated illumination of the surface by a light beam with controllable beam size (and hence controllable illumination area).

One type of optical instrument for carrying out this measurement is described in U.S. Pat. Nos. 4,710,642 (McNeil) and 5,164,790 (McNeil et al.) and in a paper by S.S.H. Naqvi et al. in the Journal of the Optical Society of America A, vol. 11, no. 9, pages 2485–2493, September 1994. FIG. 1 illustrates the basic configuration from the Naqvi et al. paper. The measurement instrument is described as an angle-scanning scatterometer in which a spot 10 on a sample 12 is illuminated by a laser beam 14 incident at an angle $\theta_i$ relative to the surface normal of the sample. Normally, the laser wavelength and incidence angle are fixed for a given measurement. Scattered light 16 is detected by a photodiode 18 over a range of scattering angles $\theta_s$ at a constant radius from the point of incidence 10 on the sample surface, as indicated by the circular detector path 20 in FIG. 1. For this purpose, the photodiode 18 may be mounted on a rotary stage (not shown) with its rotation axis passing through the illumination spot 10. In this instrument, the specularly reflected beam 22, and usually the first order diffraction beams, are removed from the data. The photodiode output may be amplified, sampled by an analog-to-digital converter, and analyzed in a microprocessor or computer 24. This apparatus, which directs a laser beam directly on the sample surface offers the advantage of being able to control the illumination area. However, the measurement is serial in nature, and therefore slow. The above-referenced '642 McNeil patent describes a variation in which a detector array, positioned in an arc extending partially around the sample, is used instead of a movable photodiode. Here, the entire range of scattering angles is detected at one time. Additional detector arrays are provided to measure the radiation of the incident beam when the sample is not in place and also to monitor the specularly reflected light to ensure proper orientation of the sample.

Figure 2:
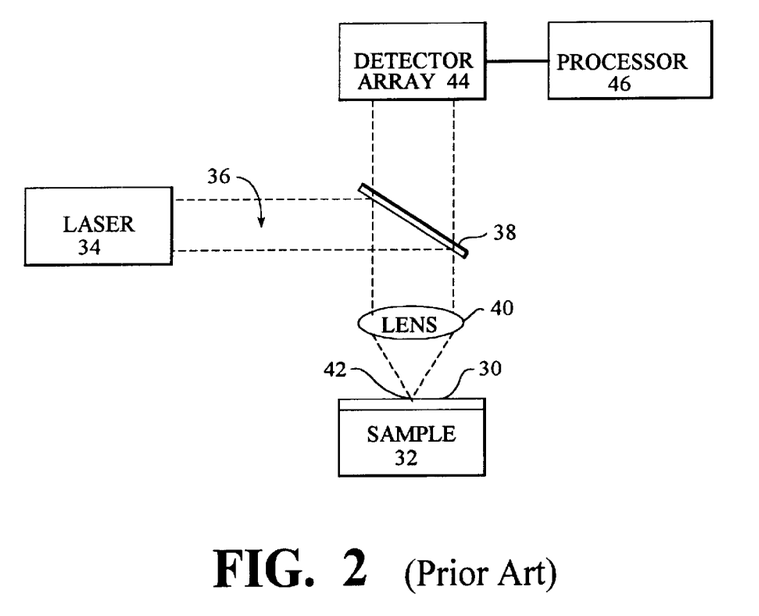
FIG. 2 is a side view diagram of a second surface inspection instrument of the prior art carrying out thin film reflectometry measurements on a sample surface with a highly focused small illumination area over a large spread of incidence angles provided by a high N.A. objective lens.

Another type of instrument employing angle-dependent intensity measurements is disclosed by Gold et al. in U.S. Pat. No. 4,999,014. FIG. 2 illustrates this configuration. There the measurements are used to determine the thickness of a thin film layer 30 on the surface of a sample substrate 32. A laser 34 generates a beam 36 that is reflected downward by a beamsplitter 38 towards the sample 32. A lens 40 having a large (at least 0.5) numerical aperture ("N.A.") focuses the beam to a spot 42 on the thin film layer 30. The N.A. of the lens 40 creates a spread of incidence angles from substantially normal to the thin film surface for the central (chief) ray to at least 30° from normal for the extreme ray. A preferred embodiment has an 0.95 N.A. lens, giving a spread of greater than 70°. The incident beam is reflected upwardly by the sample back through the lens 40, through the beamsplitter 38 and onto a photodetector array 44. Each discrete detecting element of the photodetector 44 corresponds to an incidence (and reflectance) angle at the sample surface. In a preferred embodiment there are two orthogonal linear arrays of detectors corresponding to respective S and P polarization components of the light. The intensity information obtained by the detector array 44 is used by a processor 46 to calculate the thin film thickness (and index of refraction) of the layer 30 on the sample 32. The apparatus provides parallel measurement, wherein light at many angles of incidence (and reflection) are intercepted by different elements of the detector array and detected simultaneously. In addition to providing a large angular spread for the incident and reflected light, the large N.A. lens 40 also focuses the light down to a very small spot 42 on the sample surface 30, typically on the order of 1 $\mu$m diameter or less, so that only a very small area is illuminated and highly localized variations in the sample parameters can be measured. While such a small spot is highly useful for the thin film thickness measurements for which the instrument was invented, it would be completely unsuitable when line width or other parameters are to be determined from a periodic surface structure, like a test pattern. For such a measurement, a much larger illumination area, on the order of 10 $\mu$m diameter, is required, like that provided by the instrument in FIG. 1.

Serial measurement over a 50° to 60° range of reflection angles, one degree at a time, is relatively inefficient, typically taking about a minute to complete, including the time needed to physically move the detector to each measurement position. Parallel measurement by a fixed detector array would be much faster, taking as little as a millisecond to complete. Unfortunately, the diffraction properties of light create a conflict between a high N.A. objective lens used to obtain a large range of incidence and reflection (or transmission) angles over which simultaneous measurements are taken and the large illumination area needed for measurements of a periodic test pattern on a wafer surface. The spot size of a light beam at the focus is proportional to $\lambda$/N.A., where $\lambda$ is the wavelength of the light and N.A. is the numerical aperture of the optical system. The proportionality constant is usually between 0.6 to 1.2, depending on the definition of beam size and other factors, such as the degree of coherence of the beam. It can be seen from this relationship between normal aperture and the beam size at the focus that the larger illumination areas required for periodic test patterns necessitates optics with a much smaller numerical aperture, or even direct laser beam illumination as in the instrument shown in FIG. 1, thereby reducing the range of angles over which a measurement is taken. Likewise, if large numerical aperture optics are used to obtain a larger range of incidence and reflection (or transmission) angles for simultaneous measurement, then a small illumination spot results. Illuminating a relatively large area, e.g., on the order of 10 µm diameter, is important in those measurement applications where the effects of light interaction with periodic surface structures are needed, and also where it is desired that the measurement be an average over the illumination area so as to be relatively insensitive to localized variations in the sample properties.

Accordingly, it is an object of the present invention to provide angle-dependent optical measurements simultaneously over a wide range of incidence and reflection (or transmission) angles for an illumination area that is many times larger than the diffraction limit of the objective lens.

DISCLOSURE OF THE INVENTION

The above object has been met with a reflection or transmission measurement instrument that includes an optical imaging array in the path of a collimated light beam between its light source and a high numerical aperture objective lens. The array and objective lens reconfigure the optical system into multiple apertures providing mutually spatially incoherent bundles of light to the objective lens, whereby the diffraction-dependent spot size can be controlled independently of the range of illumination angles. The individual light bundles are then focused to a common spot on the sample surface by the objective lens, with each light bundle corresponding to a particular incidence and reflection angle. The N.A. of the objective lens is preferably at least 0.7 so as to provide a range of incidence angles for the light bundles from normal (0°) to the sample surface up to 50° or more. Because the light beam has been broken up by the imaging array into light bundles, any spatial coherence in the original light beam is destroyed so as to be absent between the individual bundles of light. The common focused spot provided by the large N.A. objective lens for the many light bundles is many times larger than the area defined by the diffraction limit of the lens for a corresponding single coherent beam. In effect, the proportionality constant in the previously described relationship between spot size and numerical aperture has been substantially increased. Preferably, the common spot has a diameter of at least 10 µm, and for example can illuminate at least ten periods of a periodic surface structure on the sample surface. Thus, both a large range of illumination angles and a large illumination area is simultaneously achieved.

The measurement instrument further includes a detector array positioned to receive and detect light reflected from or transmitted through the sample surface for a range of incidence angles at the surface. In a reflectometer instrument, the reflected light passes back through the objective lens, where it is substantially collimated, passes through the individual imaging elements of the imaging array, which are aligned with corresponding light bundles of specular reflection, and then imaged onto the detector array such that each group of one or more detection elements of the detector array corresponds to a light bundle from one of the imaging elements of the imaging array and thus to a particular incidence and reflection angle. In a transmittance measuring instrument (or transmissometer), the transmitted light is collimated by a second objective lens and imaged onto the detector array which is on the opposite side of the sample surface from the illumination source. Processing means analyzes the angle-dependent reflectance or transmittance measured by the detector array to determine therefrom a desired parameter of illuminated features, such as a periodic test pattern, or the sample surface. The analysis may use either a theoretical model or measurements performed on calibration standards to arrive at the desired parameter or parameters, e.g., linewidth.

The measurement instrument may be made part of the optical head of a more comprehensive semiconductor wafer inspection apparatus. Such an apparatus would normally include a vibration isolating platform, holding a wafer stage with vacuum chuck and wafer motion elements, and which is cooperative with wafer handling equipment, such as a storage cassette and autoloader. The apparatus would further include an optical head that includes autofocus and wafer alignment sensors in addition to the reflectometer or transmissometer. Additional optical inspection and measurement devices could be included. A central processing system of the apparatus includes computer processors for controlling wafer motion by the stage as well as for acquisition and analysis of the data. An electrical power subsystem distributes power to the various electronic components and motion motors of the apparatus. The apparatus may be fully automated or allow for varying degrees of human intervention.

BEST MODE OF CARRYING OUT THE INVENTION

Figure 3:
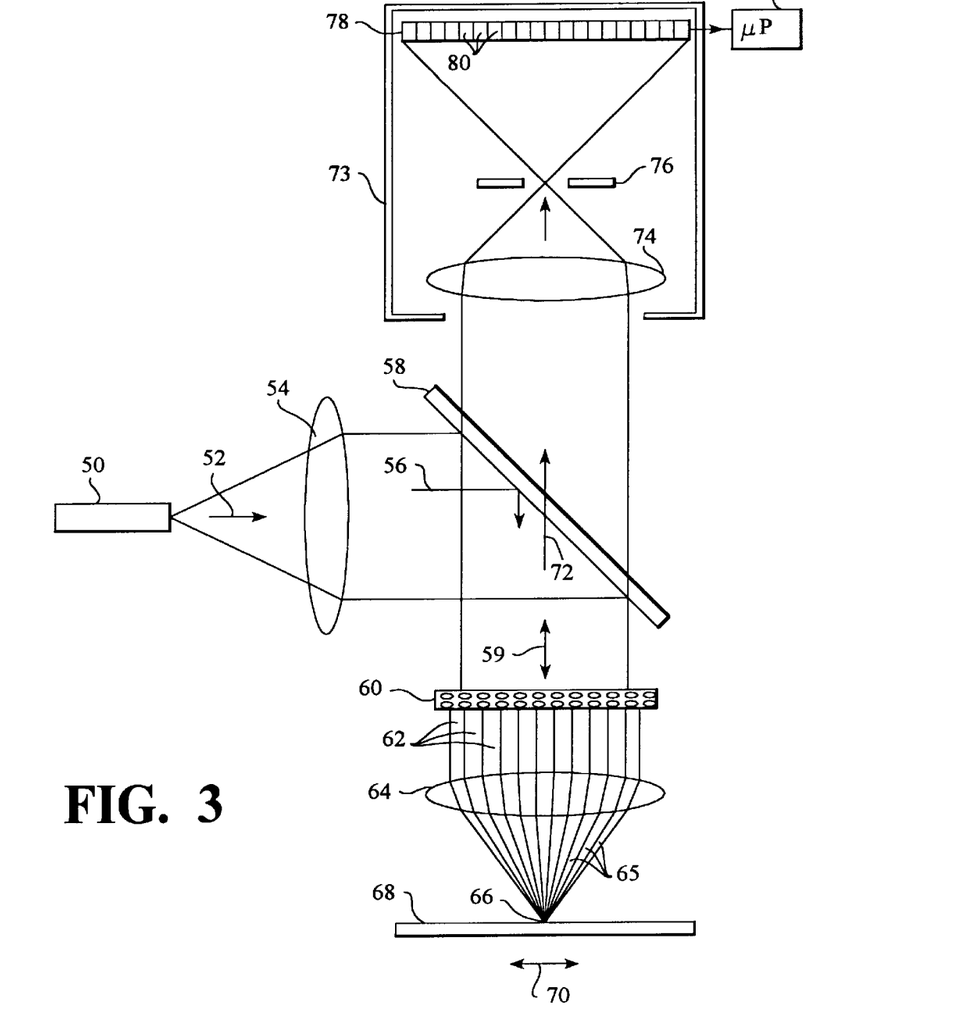
FIG. 3 is a side view diagram of a reflectometer in accord with the present invention, useful for carrying out linewidth measurements, and characterized by both a large spread of incidence angles of illumination and a large illumination area.

With reference to FIG. 3, a reflectometer instrument in accord with the present invention includes a light source 50, such as a laser, emitting a beam 52 which is either already substantially collimated or may be expanded, collimated and shaped by optics 54, such as one or more lenses. The laser light source 50 could be a He—Ne laser providing red 633 nm light, a frequency-doubled Nd:YAG laser providing green 532 nm light, a laser diode or other laser, preferably one with a visible or ultraviolet wavelength. The laser light 52 is normally monochromatic and temporally (spectrally) coherent. A stable emission wavelength is desirable. The beam should have sufficiently low intensity at the sample surface 68 so as not to damage the surface or any of the intervening optics. The collimated beam 56, having a typical diameter on the order of 1 cm or more, is reflected by a beamsplitter 58 toward the sample 68. The beamsplitter 58 may be a semitransparent mirror or a cube beamsplitter. Although only a single light source is shown, another source and beamsplitter can be added to measure reflectance at a second wavelength. For example, He-Ne lasers are available that can emit at 612, 594 or 543 nm instead of 633 nm. Alternatively, a single source with multiple selectable lasing wavelengths or a wavelength-tunable laser source could be used. For example, argon lasers can emit at 528, 514, 488 and 458 nm, etc. which are selectable as to wavelength.

Figure 4:
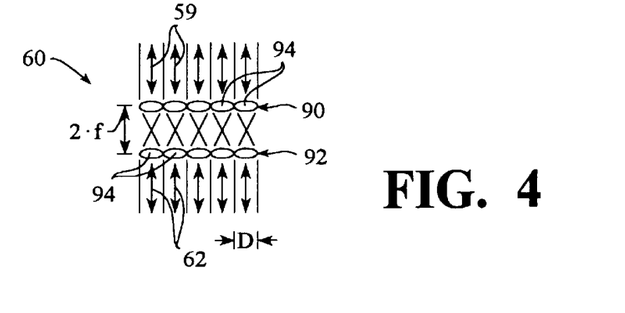
FIG. 4 is a side view of an enlarged portion of the imaging array in the reflectometer of FIG. 3.

The beam 59 passes through an imaging array 60 where it is broken up into a plurality N of individual light bundles 62. The imaging array 60 may be located in both the illuminating and collecting light paths between the beamsplitter 58 and the objective lens 64, as shown, or alternatively may be placed between the source 50 and the beamsplitter 58 so as to be out of the reflected return path. The imaging array 60 is only needed in the illuminating light path. The imaging array 60 could be a fiber bundle, with each fiber being about 1 cm long. The lengths need not be exactly the same, as any differences in length or other light propagation parameters for the different optical fibers help to destroy any spatial coherence between the individual light bundles output from the fibers of the bundle. However, a preferred imaging array 60, instead of the aforementioned fiber bundle, is a pair of lenslet arrays, as seen in FIG. 4. The light 59 first passes through a first lenslet array 90 and then through an identical second lenslet array 92. Each lenslet array 90 and 92 has a plurality N of identical small aperture lenslets 94. The diameter D of each lenslet 94 in the arrays may range from 0.1 to 1.0 mm, and is mostly a function of the desired number N of lenslets in each array and the overall width of the light beam. Typically, there are about 100 to 120 lenslets in each array. The lens material may be glass or plastic, and may either be assembled from individual lenses or formed as a single integrated unit. Such lens arrays are commercially available. For example, lens array model no. 0100-0.5-S from Adaptive Optics Associates Inc. of Cambridge, Mass. could be used. Optically equivalent, binary or holographic, diffractive optical elements may be used in place of refractive lens elements. The lenslets are mounted in a common support to maintain their relative alignment and separation. The tolerances needed are well within the level of ordinary skill. Each lenslet 94 is a positive lens with a typical focal ratio (f/D) larger than 1, so that the focal length f of each lenslet ranges from 0.1 mm to more than 1 mm. The second lenslet array 92 is aligned with the first lenslet array 90 so that the lenslets 94 form pairs with a corresponding lenslet from each array. The second array 92 is placed at a distance equal to two focal lengths (2°f) from the first array 90 so that each pair of lenslets forms a unit magnification, afocal, inverting telescope.

The light emerges from the combination of the two arrays broken into bundles of light 62 defined by the lenslet apertures of the pair of lenslet arrays. Another significant effect of this arrangement is wavefront reversal in each individual light bundle 62, wherein the subaperture wavefront of the light of each bundle is inverted between the input of the first array 90 and the output of the second array 92. This wavefront reversal acts to diminish the light's spatial coherence, in particular the coherence between the different light bundles 62, thereby allowing an increased level of control over the light spot size at the sample 68. Inherent random variations in thickness and surface figure of the lenslets 94 also introduce random wavefront phase variations and wavefront distortions that further diminish coherence.

Figure 5:
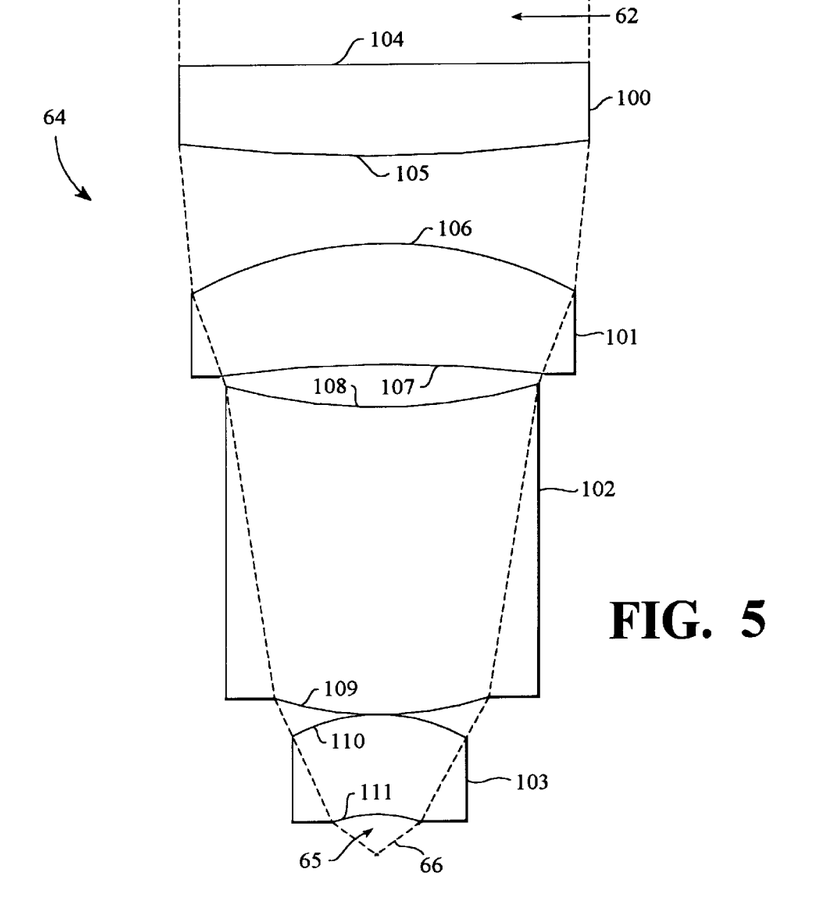
FIG. 5 is a side view of an exemplary high N.A. objective lens for use in the reflectometer of FIG. 3.

Returning to FIG. 3, the plurality of light bundles 62 are focused to a common spot 66 on the surface of sample 68 by a high numerical aperture lens 64. A high numerical aperture is defined as being at least 0.5. Preferably, the numerical aperture is at least 0.7 so as to provide a range of incidence angles at the focal spot 66 of at least up to 50 degrees. The central light bundles of the focused light 65 nearest the optical axis of the objective lens 64 have an incidence angle on the sample 68 close to normal incidence (0°), while the extreme light bundles nearest the edge of the lens 64 have a larger incidence angle near the maximum defined by the lens numerical aperture. The objective lens or lens system is commercially available from any of a number of optics houses, including Special Optics Manufacture and Design of Wharton, N.J. The objective lens 64 is usually not simply a single lens element, but rather is composed of a series of lens elements selected and positioned to be well corrected for aberrations. For example, one possible objective lens with a numerical aperture of about 0.73 is shown in FIG. 5. It is composed of four successive lens elements 100–103 defining eight lens surfaces 104–111. All four lens elements 100–103 are positive lenses. The first lens 100 is a biconvex or plano-convex lens, while the remaining three lenses are meniscus lenses, with each successive lens having somewhat larger surface curvatures than the preceding element, so as to allow the light to be gradually focused to ever greater angles after each successive lens. Spherical aberration correction is especially important so that all light bundles 65, whether central or extreme, come to a focus at a common spot 66 in the plane of the sample surface. Modern computerized optical design readily allows the lens system to be optimized for the desired numerical aperture.

Figure 6:
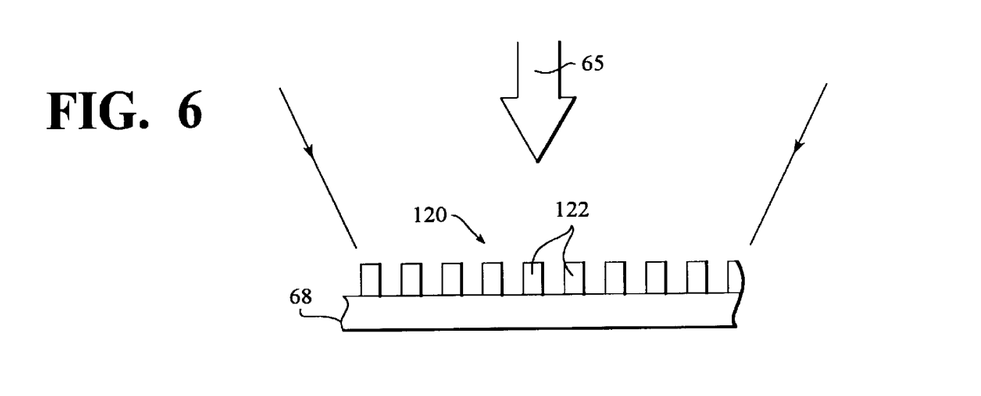
FIG. 6 is a side view of a close-up portion of a periodic surface feature on a sample surface inspected by the reflectometer of FIG. 3, illustrating an area of illumination that encompasses several periods of the surface feature.

Referring to FIG. 6, the focused light beam 65 illuminates an area of the sample 68 which may include a periodic surface structure 120, such as a test pattern with a sequence of spaced apart lines 122 of photoresist or conductive material whose parameters are to be measured. Generally, the line dimensions of the test pattern will correspond to line dimensions formed in other areas of the sample, notably those forming integrated circuits. By measuring the desired parameters for the test pattern 120, the corresponding line dimensions in other areas of the sample can be inferred with relative certainty. In the case of a periodic pattern 120 on the surface of the sample 68, the illumination area should be large enough to encompass several periods of the pattern, preferably at least 10 periods, so that an average measurement over many lines can be made. As the typical pattern has a periodicity of 1 $\mu$m or less, an illumination area on the order of 10 $\mu$m diameter or more is preferred. Even when a periodic pattern is not used, the larger illumination areas of at least 10 $\mu$m diameter are useful for obtaining an averaged reflectance measurement. Because the imaging array also modifies the irradiance distribution of the beam 56 so that it is no longer uniform when broken into bundles 62, the definition of the boundary of an illuminated spot is somewhat arbitrary. It can be defined by the region where the irradiance does not fall below about 10% of the peak irradiance near the center of the spot.

Returning to FIG. 3, light reflected from the sample returns back through the focusing objective lens 64 and is recollimated. The specularly reflected light corresponding to each incident bundle will pass through a corresponding lenslet pair of the imaging array assembly 60 on the opposite side of the system's optical axis (through the center of symmetry of the objective lens). This instrument is especially designed to work with surface structures whose periodicity is such that no diffraction orders are within the collecting cycle of the objective lens, so that the system only observes the specular reflection. The alignment tolerance to achieve passage of light bundles through corresponding lenslet pairs between incidence and reflection is 10% of the lenslet aperture or at least 1 μm, which is within the level of ordinary skill.

The light bundles 72 are partially transmitted through the beamsplitter 58 and are imaged by a CCD camera 73. The camera 73 includes a pupil imaging lens 74, a stop 76 to reduce scatter noise, and a CCD detector array 78. It is onto this detector array 78 that the light bundles from the sample surface reflection is imaged. The individual detecting elements 80 of the detector array 78 have a size that is typically about 25 to 100 μm in width. Thus, for a 1:1 correspondence between the individual light bundles 59 passing through the imaging array 60 toward the detector array 78 and the elements 80 of the detector array, the imaging lens 74 of the CCD camera 73 needs to provide a magnification ranging from about 1 to less than 1/40. Alternatively, each light bundle may be imaged onto a group of detector elements 80. A group of four detector elements 80 per light bundle is typical. A signal-to-noise ratio of about 250:1 to 300:1 is required for most applications. For relatively low reflectance samples, reducing noise from scatter and other sources may be achieved by the stop 76, and optionally a wavelength-selective bandpass filter in front of the detector array 78, as well as possibly even cooling the detector array itself. A commercially available CCD camera, such as model no. TE/CCD-576 EFT made by Princeton Instruments Inc. of Trenton, N.J., may be used. Both the imaging array 60 and the detector array 80 are normally two-dimensional arrays so that data can be collected over a full range of incidence and reflection directions (360° range of planes of incidence). This capability is advantageous because many surface features, like gratings, have preferred directions (e.g., parallel or perpendicular to surface lines). 2-D collection of reflectance data allows discrimination of these preferred directions and increases the range of analysis options that are available. Further, if the incident light is linearly polarized in some direction, 2-D collection can measure the reflectance response of the surface to different polarizations.

The detector array 78 provides reflectance data to a microprocessor 82. Each detector element 80 or group of elements corresponds to a light bundle with a particular incidence and reflectance angle at the sample surface. The data may be in the form of 12 bits per detector element, providing at least 4096 possible measured intensities from the element. The microprocessor 82 may carry out a least mean square fit to a library of stored curve families representing various possible angle-dependent reflectance responses for different sample parameters. These curves may be obtained by placing calibration standards into the apparatus and measure the real reflectance response. Alternatively, the curves may be derived from a theoretical model of angle-dependent reflectance versus linewidth and shape, etc. For example, the paper to Naqui et al., *J. Opt. Soc. Am. A* 11 (9), 2845 (1994), mentioned above, describes use of a partial least-squares (PLS) calibration method and a rigorous coupled-wave theory (RCWT) model to obtain theoretical scatterograms for different line thicknesses. Line widths can be obtained from the same model. U.S. Pat. No. 5,164,790 to McNeil et al. compares results obtained using a perfectly conducting model with those obtained from coupled wave analysis, and finds excellent agreement between the two. Other theoretical models and methods might also be used. The apparatus is thus useful for analyzing a variety of parameters of surface structures on a sample, such as linewidth or shape on a wafer surface.

Figure 7:
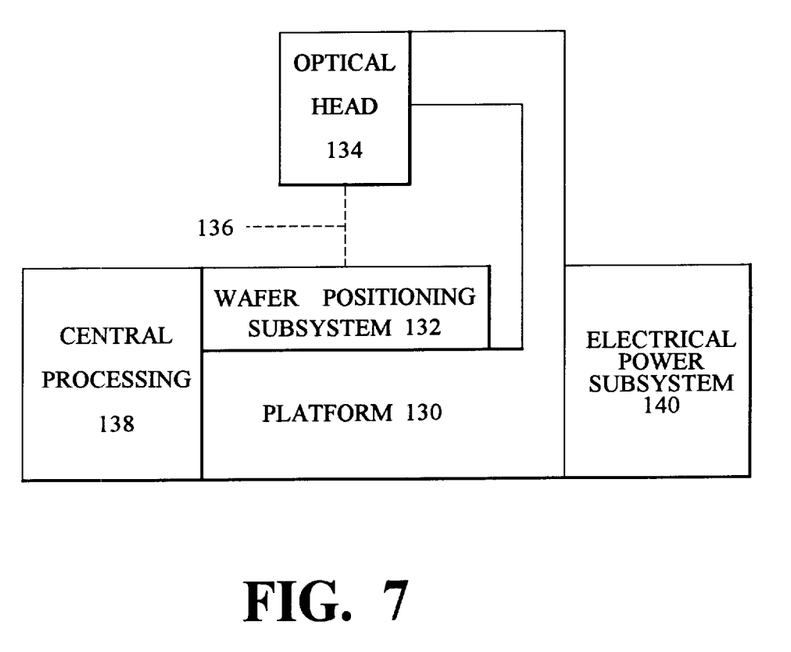
FIG. 7 is a side view block diagram showing various components of a wafer inspection apparatus that can incorporate the reflectometry instrument of the present invention as part of its optical head.

With reference to FIG. 7, a practical apparatus for semiconductor wafer metrology integrates the angle-dependent reflectometer of the present invention within a machine that automates the measurement process. The apparatus can repeat the desired measurement or measurements at many pre-programmed locations on a wafer, and on many wafers, at a high rate with minimal intervention on the part of a human operator. The apparatus includes a platform 130, which is a stable table that provides isolation from floor vibrations by means of springs or pneumatic isolators. The platform 130 holds a wafer positioning subsystem 132 and an optical head 134 containing the reflectometer. Relative motion between those two elements 132 and 134 is held by the platform 130 during measurements to less than 2 to 5 micrometers. The platform 130 can also include means for moving the optical head 134 up and down relative to the wafer positioning assembly 132 to allow for unobstructed loading or unloading of a wafer by a wafer handler and also to provide coarse focusing in order to accommodate wafers of various thicknesses.

The apparatus' wafer positioning subsystem 132 includes or cooperates with wafer handling equipment for loading and unloading wafers onto the machine. The wafer handling equipment includes one or more wafer storage cassettes and an autoloader assembly that moves wafers between the storage cassettes and a stage. The autoloader usually forms an integral part of the overall instrument. The cassettes are typically provided separately. The wafer positioning subsystem 132 further includes a stage assembly with a vacuum chuck that holds a wafer securely and a combination of motors and slides that produce precise motion of the stage in at least two, and preferably three, axes. Fine z-axis motion (up and down), if not provided by the stage, can be provided by the optical head 134. The stage may also provide for rotational motion of the wafer.

Wafer positioning is the result of cooperation between the wafer positioning subsystem 132, a wafer alignment sensor in the optical head 134, and motion control provided by a central processing system 138. The alignment sensor is a low magnification (about 1× to 6×) camera that images a small illuminated area of a semiconductor die on the wafer. A motion control processor in the central processing system 138 receives image data from the alignment sensor, employs pattern recognition algorithms to identify unique alignment marks or recognizable pattern features on the wafer, and then controls the motion motors of the stage to automatically position the wafer at an initial point and align it with the axes of motion. The wafer can then be navigated to designated measurement positions for that wafer. A template matching technique like that described by Ramesh Jain, et al. in the book *Machine Vision*, published by McGraw-Hill Inc. (1995), section 15.6.1, pages 482–483, can be used to recognize a wafer's alignment mark. Measurement points relative to an initial wafer position can be designated by a user for a particular class of wafers to be inspected.

The optical head 134 includes all of the elements of the reflectometry instrument of FIG. 3 and is in optical communication 136 with the wafer on the positioning subsystem's stage. In addition, it includes the wafer alignment sensor (camera) that aids the wafer positioning subsystem 132. Further, the optical head 134 includes a focus sensor that enables automatic focusing. One commonly used focus sensor uses a light source that is focused on the wafer surface at an angle. The reflected light is detected by a bi-cell detector. As the focus varies, the detected beam will translate across the bi-cell. This type of autofocus system is described by D. H. Kim et al. in *Proceedings SPIE*, vol. 2726, pages 876–885 (1996). The three optical head elements, reflectometer, alignment sensor and autofocus sensor, are not optically integrated, but are physically mounted together within a single unit and have a common focus condition. While the alignment sensor normally images a slightly different location than the spot illuminated by the reflectometer, the lateral displacement is fixed and can be taken into account when positioning the wafer for measurement. Likewise, even if the autofocus sensor were to use a slightly different location on the wafer for determining the focus condition, the wafer is sufficiently flat that focus would be within the required focus tolerance for the reflectometer.

An electrical power subsystem 140 includes one or more power supplies and distribution cables to provide AC and DC power to the electronic components and motion motors of the apparatus.

The central processing system 138 includes one or more computer processors for digital motion control of the wafer positioning system 132 stage and of the optical head 134 and for data acquisition and analysis. For example, there may be several processors which are each dedicated to a particular function and a main or host processor for coordinating the separate processors. Moreover, there may be one or more data ports and a network interface processor for possible interaction via a network with a factory computer. The central processing system 132 also includes memory for storing designated measurement locations as well as actual measurement data and the analysis results.

The overall metrology apparatus provides effective automated reflectometry measurements and analysis of many wafers. The improved reflectometer improves speed and accuracy by allowing parallel measurement at many incidence and reflectance angles through a high numerical aperture objective lens and a detector array, while maintaining control over illuminated spot size by means of the imaging array. Large spot sizes allow averaged measurements and measurements of periodic wafer surface structures to be obtained.

Figure 8:
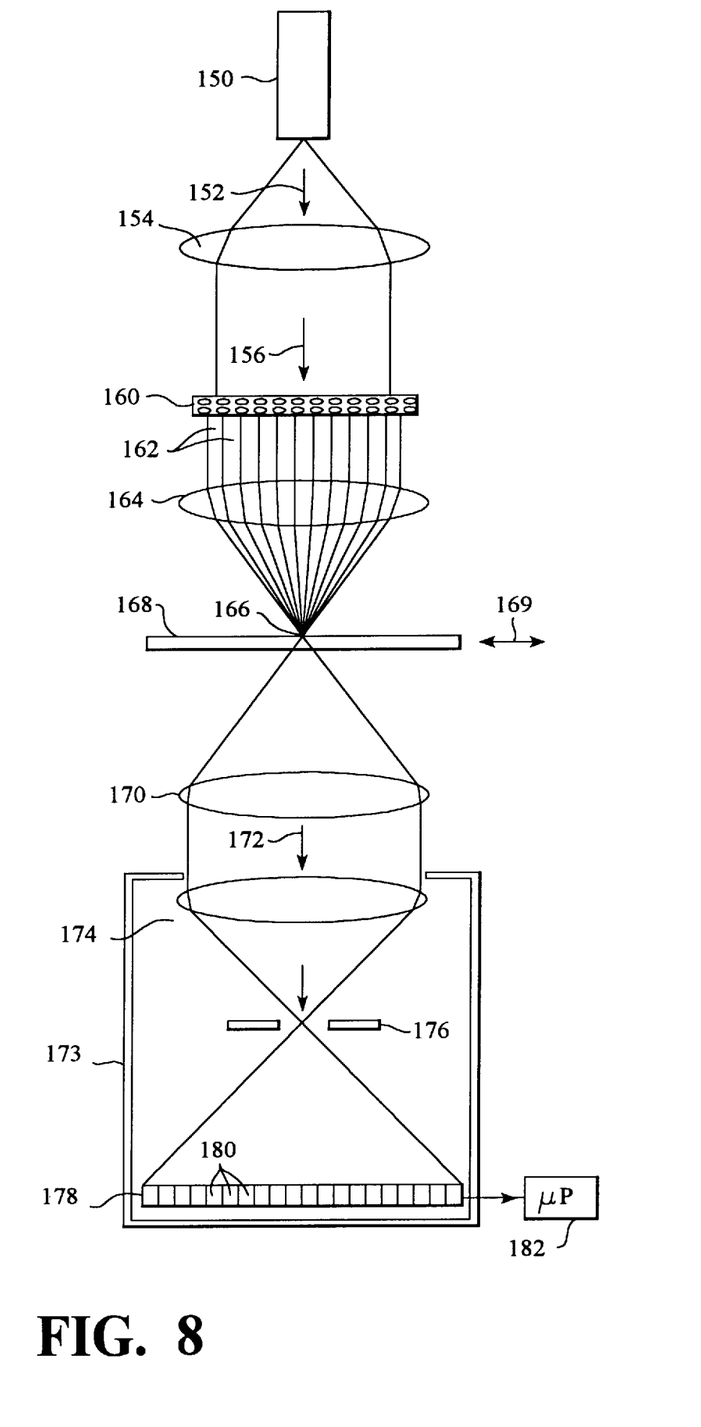
FIG. 8 is a side view diagram of a transmissometer embodiment in accord with the present invention.

With reference to FIG. 8, instead of the reflectometer instrument of FIG. 3, an analogous transmissometer instrument can be constructed in accord with the present invention. Like the reflectometer instrument, the transmissometer in FIG. 8 can illuminate a common spot on a sample surface with a spot size that is several times larger than the diffraction limit for coherent light beams, e.g. a diameter of 10 μm or more, with a wide range of simultaneous incidence angles at the sample surface, and can then collect and detect the light, in this case transmitted through the sample (e.g., a photomask or reticle), so as to determine dimensions of surface features formed on the sample being inspected. This instrument includes a light source 150, such as a laser, like the light source 50 of the reflectometer in FIG. 3. The light source 150 emits a beam 152 which may be expanded, shaped and collimated by optics 154 to form the collimated beam 156. The beam 156 passes through an imaging array 160, essentially identical to the imaging array 60 in FIGS. 3 and 4, where the beam 156 is broken up into a plurality N of individual, mutually spatially incoherent, light bundles 162. The plurality of light bundles 162 are focused to a common spot 166 on a sample surface 168 by means of a high numerical aperture objective lens 164. The sample 168 may be moved relative to the location of the spot 166, as indicated by arrow 169, in order to illuminate different desired areas of the sample surface. Light transmitted through the sample 168 is collected by another high numerical aperture (at least 0.5) objective lens 170 which can be, and usually is, identical to the focusing objective lens 164. However, identical lenses 164 and 170 are not essential. What matters is that lens 164 provides a large range of incidence angles for the different beamlets 162 at the illumination spot, while the lens 170 allows light collection over a wide range of transmission angles. A collection lens 170 with a numerical aperture at least as large as the focusing lens 164 allows collection of transmitted light corresponding to all of the incidence angles. A lens system like that shown in FIG. 5 can be used for either or both lenses 164 and 170. A second imaging array like array 160 is not required in the transmitted light path. The collected light 172 is received by a CCD camera 173 like the camera 73 in the reflectometer of FIG. 3. The camera 173 is located optically, but not necessarily physically, on the transmitted side of the sample 168 opposite the side containing the illumination source 150. It is well known that light paths can be folded for compactness, so that the source and camera might be physically adjacent. The camera 173 includes a pupil imaging lens 174, a stop 176 to reduce scatter noise and a CCD detector array 178 with a plurality of detecting elements 180. Each detector element 180, or group of such elements, corresponds to a light bundle 162 with a particular incidence angle and transmission angle through the sample 168 at the spot 166. The detector array 178 thus provides angle-dependent transmittance data to a microprocessor 182. As in the case with reflectometry, the transmittance data may be analyzed by comparison with a library of expected transmittance responses for various parameters of interest, derived from calibration standards or theoretical models, in order to obtain one or more desired dimensions of features on the sample 168. The apparatus of FIG. 7 can be readily adapted to include the transmissometer of FIG. 8, if desired.

I claim:

1. A reflectometer, comprising a light source providing a collimated light beam directed along a path, an optical imaging array in the path of said collimated light beam, said imaging array including a plurality N of individual imaging elements, each element receiving a portion of said collimated light beam, the imaging array breaking the collimated light beam into N individual light bundles, an objective lens in the path of said light bundles for focusing said bundles to a common spot on a sample surface, said objective lens and said optical imaging array also in the path of light reflected from said spot on said sample surface for collecting and imaging said reflected light, and a detector array positioned to receive from said optical imaging array and detect reflected light corresponding to a range of incidence angles at said sample surface.

2. The reflectometer of claim 1 wherein the objective lens has a numerical aperture of at least 0.5.

3. The reflectometer of claim 1 wherein the common spot of said light bundles focused onto said sample surface has a diameter of at least 10 μm, and the light bundles have a range on incidence angles on the sample surface from perpendicular to said surface (0°) to at least 50° from perpendicular.

4. The reflectometer of claim 1 wherein the common spot of said light bundles focused onto said sample surface has a size that illuminates at least ten periods of a periodic pattern on said surface.

5. A reflectometer, comprising a light source providing a collimated light beam directed along a path, an optical imaging array in the path of said collimated light beam, said imaging array including a plurality N of individual imaging elements, each element receiving a portion of said collimated light beam, the imaging array breaking the collimated light beam into N individual light bundles, an objective lens in the path of said light bundles for focusing said bundles to a common spot on a sample surface, and also in the path of light reflected from said spot on said sample surface for collecting said reflected light, and a detector array positioned to receive and detect reflected light corresponding to a range of incidence angles at said sample surface, wherein said imaging array comprises a pair of identical lenslet arrays positioned two focal lengths apart with corresponding lenslets in said pair of lenslet arrays being aligned with one another, each corresponding pair of aligned lenslets of the respective lenslet arrays forming an individual imaging element of the imaging array.

6. The reflectometer of claim 1 wherein said imaging array comprises an optical fiber imaging bundle, each optical fiber of said bundle forming one of said individual imaging elements of the imaging array and maintaining an ordered correspondence between the individual light bundles passing through the imaging array from entry to exit of the optical fibers toward the detector array.

7. The reflectometer of claim 1 wherein said detector array has a plurality of detection elements, such that each group of at least one detection element of said detector array receives light corresponding to a particular incidence and reflection angle of light illuminating said sample surface, whereby said detector array provides a measure of reflectance from said sample surface over a range of incidence angles.

8. The reflectometer of claim 1 wherein said imaging array and said detector array are two-dimensional arrays.

9. The reflectometer of claim 1 further comprising processing means in communication with said detector array for analyzing measured reflectance versus incidence angle received from said detector array and determining therefrom a desired characteristic parameter of the illuminated area of said sample surface.

10. The reflectometer of claim 9 wherein said processing means includes comparison means fitting said measured reflectance versus incidence angle to one best curve of a library of stored curve families representing possible reflectance responses for different values of said desired characteristic parameter.

11. A reflectometer, comprising a laser providing a collimated light beam directed along a path, an optical imaging array in the path of said collimated light beam, said imaging array including a plurality N of individual imaging elements, each element receiving a portion of said collimated light beam, the imaging array breaking the collimated light beam into N individual light bundles, wherein spatial coherence in said collimated light beam is absent between said individual light bundles, a high numerical aperture objective lens in the path of said light bundles for focusing said bundles to a common spot on a sample surface, the objective lens having a numerical aperture of at least 0.5, the common spot having a diameter of at least 10 $\mu$m, whereby any periodic pattern on said sample surface is illuminated over at least 10 periods of said periodic pattern and over a range of incidence angles of said light bundles, a detector array positioned to receive and detect light reflected from said sample surface through said objective lens and said imaging array, each group of at least one detection element of said detector array corresponding to and receiving light from an individual imaging element of said imaging array and corresponding to an incidence angle of light on said sample surface, whereby said detection array provides a measure of reflectance from said periodic pattern versus incidence angle over said range of incidence angles, and processing means for analyzing said measure of reflectance versus incidence angle received from said detector array and determining therefrom a desired parameter of said periodic pattern on said sample surface.

12. The reflectometer of claim 11 wherein said imaging array is a pair of identical lenslet arrays positioned two focal lengths apart with corresponding lenslets in said pair of arrays aligned with one another, each corresponding pair of aligned lenslets forming an individual imaging element of said imaging array.

13. The reflectometer of claim 11 wherein said imaging array is a fiber bundle, each optical fiber in said bundle forming one of said individual imaging elements of said imaging array.

14. The reflectometer of claim 11 wherein said imaging array and said detector array are two-dimensional arrays.

15. A surface inspection apparatus, comprising:

a vibration-isolation platform holding an object having a surface to be inspected on a stage and an optical head in relative optical communication therewith, the optical head including a reflectometer;

means operative on the stage and said optical head for controlling relative motion between said stage and optical head, such that said reflectometer measures angle-dependent reflectance at selected locations of the surface on said stage; and processing means for analyzing reflectance data obtained from said reflectometer and determining therefrom a desired characteristic parameter at said selected locations of said surface;

wherein said reflectometer includes (a) a light source providing a collimated light beam directed along a path, (b) an optical imaging array in the path of said collimated light beam, said imaging array having a plurality N of individual imaging elements, each imaging element receiving a portion of said collimated light beam, the imaging array breaking the collimated light beam into N individual light bundles, wherein any spatial coherence in said collimated light beam is absent between said individual light bundles (c) an objective lens in the path of said light bundles focusing the light bundles to a common spot on a selected location of the surface, the objective lens and the optical imaging array also being in the path of light reflected from said spot on said surface for collecting and imaging said reflected light, and (d) a detector array positioned to receive from said imaging array and detect reflected light corresponding to a range of incidence angles at said surface, said detector array connected to said processing means so as to deliver angle-dependent reflectance data thereto.

16. The apparatus of claim 15 wherein said means for controlling motion includes (i) a camera in the optical head observing an area of a wafer on the stage in a known fixed lateral displacement from the location of said common spot for said reflectometer, (ii) additional processing means receiving an image of said observed area from said camera for identifying at least one alignment mark on the observed wafer and for controlling navigation motion of the wafer by said stage to said successive selected locations, the additional processing means having memory means for storing said selected locations therein, and (iii) motion motors of said stage responsive to said additional processing means for moving said wafer in accord with said controlled navigation motion to said selected locations.

17. The apparatus of claim 15 further having autofocus means in the optical head for adjusting a focus of the objective lens of said reflectometer relative to the surface.

18. The apparatus of claim 15 wherein the processing means for analyzing reflectance data includes comparison means fitting the angle-dependent reflectance to one best curve of a library of stored curve families representing possible reflectance responses for different values of said desired characteristic parameter.

19. The apparatus of claim 15 wherein the common spot of the light bundles focused by the objective lens of the reflectometer onto the selected locations on the surface has a diameter of at least 10 $\mu$m, and the light bundles have a range of incidence angles on the surface from perpendicular to said surface (0°) to at least 50° from perpendicular.

20. The apparatus of claim 15 wherein the selected locations on the surface include a periodic surface pattern, the common spot of the light bundles focused by the objective lens of the reflectometer onto the sample surface having a size that illuminates at least ten periods of the periodic surface pattern.

21. A surface inspection apparatus, comprising:
a vibration-isolation platform holding an object having a surface to be inspected on a stare and an optical head in relative optical communication therewith. the optical head including a reflectometer;
means operative on the stage and said optical head for controlling relative motion between said stage and optical head, such that said reflectometer measures angle-dependent reflectance at selected locations on the surface while on said stage; and
processing means for analyzing reflectance data obtained from said reflectometer and determining therefrom a desired characteristic parameter at said selected locations of said surface;
wherein said reflectometer includes (a) a light source providing a collimated light beam directed along a path, (b) an optical imaging array in the path of said collimated light beam, said imaging array having a plurality N of individual imaging elements, each imaging element receiving a portion of said collimated light beam, the imaging array breaking the collimated light beam into N individual light bundles, (c) an objective lens in the path of said light bundles focusing the light bundles to a common spot on a selected location of the surface, and (d) a detector array positioned to receive and detect reflected light corresponding to a range of incidence angles at said surface, said detector array connected to said processing means so as to deliver angle-dependent reflectance data thereto,
wherein the imaging array of the reflectometer comprises a pair of identical lenslet arrays positioned two focal lengths apart with corresponding lenslets in said pair of lenslet arrays being aligned with one another, each corresponding pair of aligned lenslets of the respective lenslet arrays forming an individual imaging element of the imaging array.

22. The apparatus of claim 15 wherein said object is a semiconductor wafer.

23. A transmissometer, comprising
a light source providing a collimated light beam directed along a path,
an optical imaging array in the path of said collimated light beam, said imaging array including a plurality N of individual imaging elements, each element receiving a portion of said collimated light beam, the image array breaking the collimated light beam into N individual light bundles, wherein any spatial coherence in said collimated light beam is absent between said individual light bundles,
a first objective lens in the path of said light bundles for focusing said bundles to a common spot on a sample surface, wherein the common spot of light bundles focused into said sample surface has a diameter of at least 10 $\mu$m, and the light bundles have a range of incidence angles on the sample surface from perpendicular to said surface (0°) to at least 50° from perpendicular,
a second objective lens in a path of light transmitted through said sample surface from said spot for collecting said transmitted light, and
a detector array positioned to receive and detect transmitted light from said second objective lens, the received and detected transmitted light corresponding to a range of incidence angles at said sample surface, wherein said detector array has a plurality of detection elements such that each group of at least one detection element of said detector array receives light corresponding to a particular incidence and transmission angle of light illuminating said sample surface, whereby said detector array provides a measure of transmittance through said sample surface over a range of incidence angles.

24. The transmissometer of claim 23 wherein said first and second objective lenses both have numerical apertures of at least 0.5.

25. A transmissometer, comprising
a light source providing a collimated light beam directed along a path,
an optical imaging array in the path of said collimated light beam, said imaging array including a plurality N of individual imaging elements, each element receiving a portion of said collimated light beam, the image array breaking the collimated light beam into N individual light bundles,
a first objective lens in the path of said light bundles for focusing said bundles to a common spot on a sample surface,
a second objective lens in a path of light transmitted through said sample surface from said spot for collecting said transmitted light, and
a detector array positioned to receive and detect transmitted light from said second objective lens, the received and detected transmitted light corresponding to a range of incidence angles at said sample surface, wherein said imaging array comprises a pair of identical lenslet arrays positioned two focal lengths apart with corresponding lenslets in said pair of lenslet arrays being aligned with one another, each corresponding pair of aligned lenslets of the respective lenslet arrays forming an individual imaging element of the imaging array.

26. The transmissometer of claim 23 wherein said imaging array comprises an optical fiber bundle, each optical fiber of said bundle forming one of said individual imaging elements of the imaging array.

27. The transmissometer of claim 23 wherein said imaging array and said detector array are two-dimensional arrays.

28. The transmissometer of claim 23 further comprising processing means in communication with said detector array for analyzing measured transmittance versus incidence angle received from said detector array and determining therefrom a desired characteristic parameter of the illuminated area of said sample surface.

29. The transmissometer of claim 28 wherein said processing means includes comparison means fitting said measured transmittance versus incidence angle to one best curve of a library of stored curve families representing possible transmittance responses for different values of said desired characteristic parameter.

30. A method of obtaining simultaneous measurement of angle-dependent specular reflectance over a range of incidence and reflection angles, comprising providing a collimated light beam and directing said beam along a path, breaking said beam into a plurality of individual light bundles, wherein any spatial coherence in said collimated light beam is absent between said individual light bundles, focusing said bundles to a common spot on a sample surface, said spot having a size that is substantially larger than a diffraction-limited spot size for a focused spatially coherent beam, said focused light bundles having a range of incidence angles on said sample surface, collecting light reflected from said spot on said sample surface, the reflected light being collected over a range of reflection angles comparable to said range of incidence angles, and detecting said reflected light corresponding to the different reflection angles within said range of reflection angles, the detection providing an angle-dependent measurement of reflectance from said sample surface.

31. The method of claim 30 wherein said range of incidence angles for said focused light bundles and said range of reflection angles for said collected light extend from perpendicular to said sample surface (0°) to at least 50° from perpendicular.

32. The method of claim 30 wherein said light bundles are focused to a spot having a diameter of at least 10 $\mu$m.

33. The method of claim 30 wherein breaking said collimated light beam into individual light bundles includes directing said light beam through an imaging array, where each element of said imaging array receives and inverts a different portion of said light beam.

34. The method of claim 30 wherein breaking said collimated light beam into individual light bundles includes directing said light beam through a bundle of optical fibers.

35. The method of claim 30 wherein focusing said light bundles to a common spot and collecting said reflected light comprises directing said light bundles through an objective lens in a first direction and passing said reflected light back through said objective lens in a second direction.

36. The method of claim 30 wherein said collimated light beam is broken into a two-dimensional array of individual light bundles and detecting said reflected light is accomplished by a two-dimensional detector array, whereby reflectance in different planes of incidence can be measured.

37. The method of claim 30 further comprising analyzing measured angle-dependent reflectance data to determine a desired characteristic parameter of the illuminated spot on said sample surface.

38. The method of claim 37 wherein analyzing said data includes comparing said angle-dependent reflectance data with a library of stored reflectance data corresponding to known values of said desired characteristic parameter.

* * * * *

UNITED STATES PATENT AND TRADEMARK OFFICE
CERTIFICATE OF CORRECTION

PATENT NO : 5,889,593
DATED : March 30, 1999
INVENTOR(S) : Noah Bareket

It is certified that error appears in the above-identified patent and that said Letters Patent is hereby corrected as shown below:

Claim 21, col. 13, line 44, "on a stare" should be - - on a stage - -.

Signed and Sealed this

Eighth Day of February, 2000

Attest:

Q. TODD DICKINSON

Attesting Officer    Commissioner of Patents and Trademarks